United States Patent

Ahola et al.

Patent Number: 6,001,115
Date of Patent: Dec. 14, 1999

[54] BLADE GUARD FOR A SURGICAL TOOL

[75] Inventors: Jon J. Ahola, Kalamazoo; Douglas G. Harris, Portage, both of Mich.

[73] Assignee: Stryker Corporation, Kalamazoo, Mich.

[21] Appl. No.: 09/120,094

[22] Filed: Jul. 21, 1998

[51] Int. Cl.[6] .................................................. A61B 17/14
[52] U.S. Cl. ............................................ 606/176; 606/82
[58] Field of Search ................................... 606/176, 177, 606/82, 172, 178, 179; 128/898

[56] References Cited

U.S. PATENT DOCUMENTS

| | | | |
|---|---|---|---|
| 2,367,432 | 1/1945 | Reprogle | 606/176 |
| 5,433,457 | 7/1995 | Wright | 606/177 |
| 5,609,603 | 3/1997 | Linden | 606/177 |
| 5,913,869 | 6/1999 | Reil | 606/185 |

OTHER PUBLICATIONS

Manufacturing drawing for Stryker Blade Guard, Part No. 0298–097–008, Sep., 1986.
*The Hall Thoracic Surgery System* Product Brochure, Jan., 1991 (6 pages).

*Primary Examiner*—Michael Buiz
*Assistant Examiner*—Kevin Truong
*Attorney, Agent, or Firm*—Flynn, Thiel, Boutell & Tanis, P.C.

[57] ABSTRACT

A blade guard (12) for preventing a saw blade (16) or other cutting member from cutting into tissue the cutting member is not intended to cut. The blade guard includes a body (20) that is attached to the surgical tool (10) from which the cutting member extends. A leg (24) extends from the body. A foot (34) is attached to the end of the leg. The foot encapsulates the end of the cutting member to prevent it from penetrating into tissue the cutting member is not intended to cut. The leg is formed with a tapered profile such that it has a leading edge (29) adjacent the cutting member that is narrow in width than the trailing edge (30) spaced from the cutting member. The tapered profile of the leg provides the leg with structural strength. The tapered profile also facilitates the separation of the sections of the bone that define the kerf as the cutting member and blade guard pass through the bone.

22 Claims, 4 Drawing Sheets

BLADE GUARD FOR A SURGICAL TOOL

FIELD OF THE INVENTION

This invention relates generally to a blade guard employed to prevent a surgical saw blade from cutting tissue other than the tissue the blade is intended to cut. More particularly, this invention relates to a blade guard that both resists deformation and assists in the separation of the tissue the complementary saw blade is employed to cut.

BACKGROUND OF THE INVENTION

The powered surgical saw has evolved into an important surgical tool. A typical powered surgical saw includes a motor that, through a drive mechanism, causes a complementary blade to move in a repeating pattern. Powered surgical saws have become very efficient tools for cutting into both hard tissue, commonly referred to as bone, and soft tissue.

When a surgical saw is used, it should only cut the tissue it is intended to cut; the saw blade should not cut into the surrounding tissue. A class of saw accessories, referred to as blade guards, prevent a surgical saw blade from penetrating tissue other than that the blade is intended to cut. One particular blade guard has been developed for use with a sternum saw. The sternum is the bone that extends down the front of the chest of an individual. The sternum is the bone that covers organs such as the thorax and heart as well as parts of the lungs and liver. In order to gain access to these soft tissue organs, the sternum saw is employed to cut and separate the sternum. The complementary blade guard prevents the end of the blade from penetrating the underlying soft tissue organs. A typical sternum guard is a one-piece unit that has three separate components. The first of these components is the body. This is the component that connects the blade guard to the complementary saw with which it is used. The second component is an elongated leg. The leg extends outwardly from the body and is positioned behind the trailing edge of the associated saw blade. A foot is connected to the distal end of the leg. The foot extends forward from the leg and is formed with an opening in which the end of the blade is located. The leg and foot are dimensioned so that, during actuation of the blade, the blade does not extend out of either the distal or proximal ends of the foot. Since the end of the blade is encapsulated in the foot, the possibility that the blade will inadvertently cut any of the tissue underneath the sternum is essentially eliminated.

While current blade guards prevent the unintended cutting of tissue by the ends of the blades with which they are used, there are some disadvantages associated with their use. Some current blade guards are provided with legs that are formed out of thin, flat pieces of metal. This is because the space in which a blade guard travels, the kerf in the bone cut by the blade, is itself relatively narrow. For example, some sternum blade have thickness ranging between 36 to 44 mils (0.036 to 0.044 inches). The associated legs are often constructed to be approximately 25 mils thick. The reason the blade guard legs are even thinner than the blades themselves is that, during surgery, the surrounding tissue has a tendency to move the separated sections of the sternum back together. Moreover, sometimes a surgeon cuts the bone so that the kerf has a non-linear profile. Owing to the curved or angled profile of these kerfs, it can be difficult to maneuver a flat blade guard through them. Therefore, to ensure that the leg can freely travel in the kerf, the leg should be thinner than the saw blade that forms the kerf.

A problem with making a leg this thin is that it is structurally a weak component. Consequently, if a leg is subjected to significant lateral pressure, it is prone to bend. Such bending naturally causes the associated foot to move out of alignment with the blade with which the blade guard is intended for use. Also, once this misalignment occurs, the blade guard may strike the blade. Also as a result of misalignment, the blade guard may bear against the bone. Once either of these events occur, significant heat may be generated at the blade guard-blade or blade guard-bone interface. Should the blade guard abut the moving blade, a significant amount of noise may also be generated. Moreover, in some circumstances, the pressing of the blade guard against either the blade or the bone may inhibit the cutting action of the surgical tool. Thus, once a blade guard falls out of alignment with the associated blade, the blade guard may no longer be useful for its intended purpose.

SUMMARY OF THE INVENTION

This invention is directed to a blade guard useful for preventing the end of a surgical cutting member, such as a saw blade, from penetrating into tissue it is not intended to cut. More specifically, the blade guard of this invention has a leg that, while dimensioned to be fit into a narrow width kerf, has significant structural strength. The leg of this invention is also configured to hold the sections of the separated bone between which it is inserted apart from each other to facilitate the further cutting of the bone.

BRIEF DESCRIPTION OF THE DRAWINGS

This invention is pointed out with particularity in the claims. The above and further features of this invention may be better understood by reference to the following description taken in conjunction with the accompanying drawings, in which:

DETAILED DESCRIPTION

Figure 1:
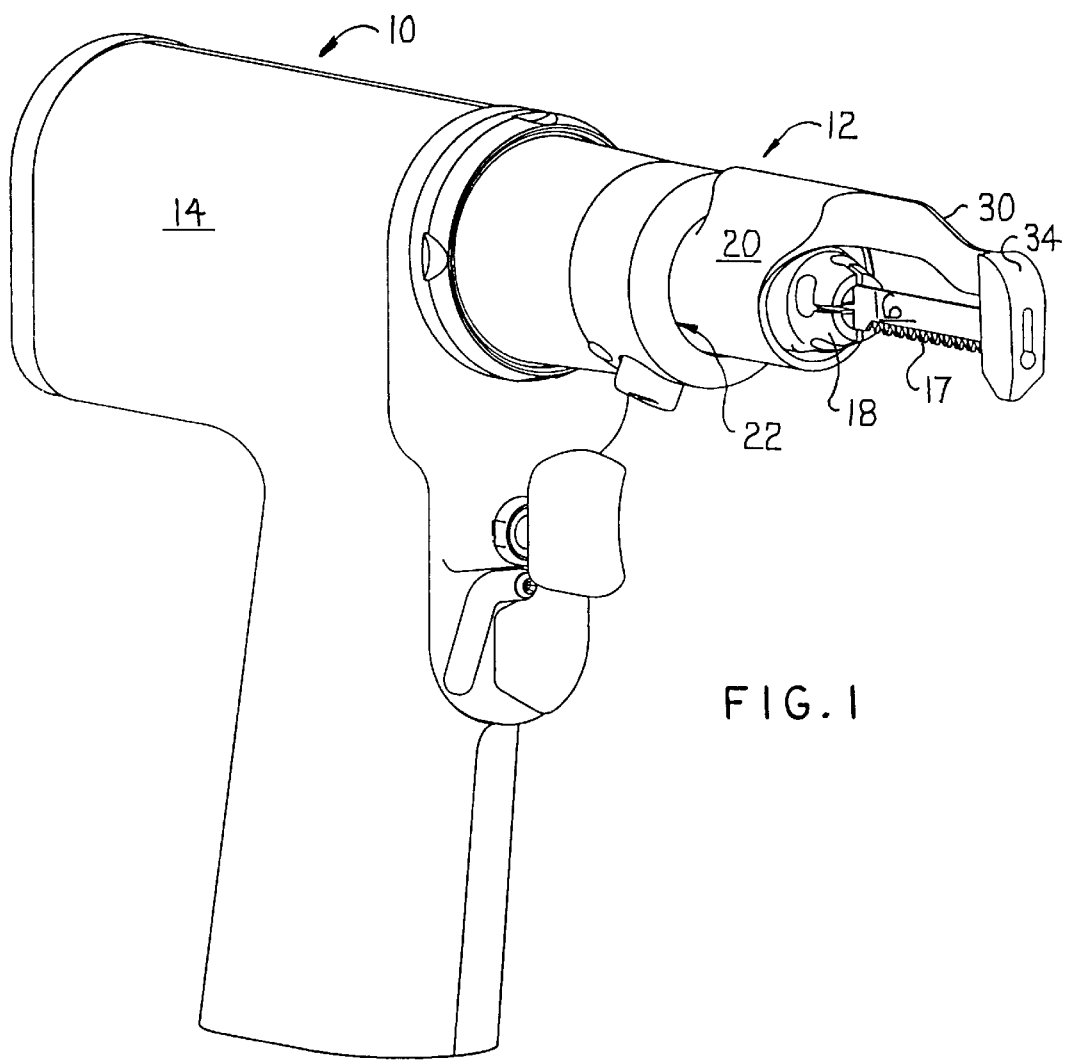
FIG. 1 is a perspective view of a surgical saw to which the blade guard of this invention is attached.

FIG. 1 depicts a surgical saw 10 to which the blade guard 12 of this invention is attached. The saw 10 includes a handpiece 14 in which a motor, (not illustrated) is housed. A saw blade 16 extends out of a chuck 18 housed in a head end of the handpiece 14. A drive train assembly, (not illustrated) connects the motor to the saw blade 16 so that when the motor is actuated, the saw blade moves in a back-and-forth reciprocating pattern along the longitudinal axis of the blade. The blade 16 has a leading edge formed to define teeth 17 that cut into tissue the saw 10 is employed to separate.

Figure 2:
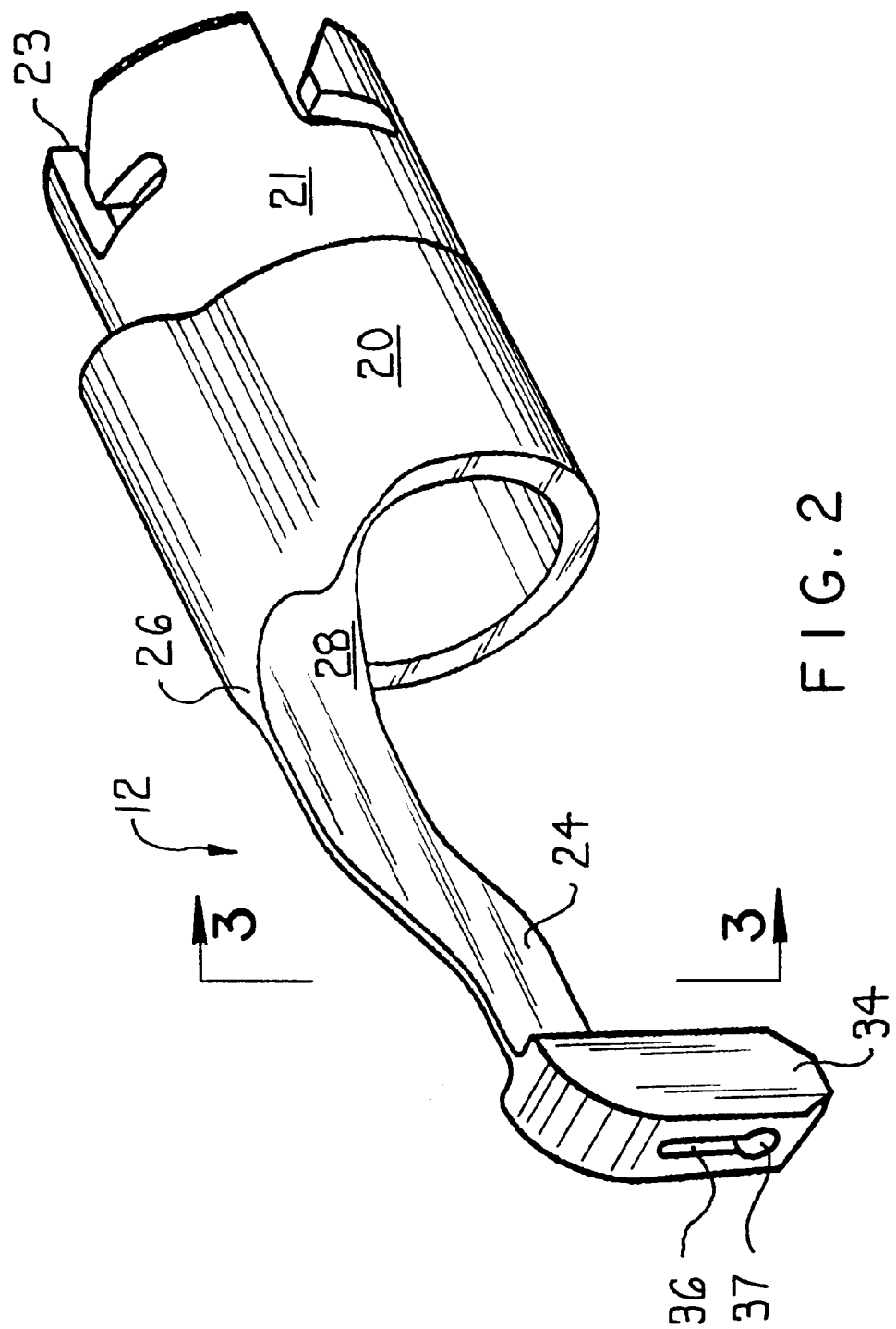
FIG. 2 is a perspective view of the blade guard.

The blade guard 12 is mounted to the head end of handpiece 14 to prevent the exposed end of the saw blade 16 from penetrating into tissue it is not intended to cut. As seen by reference to FIGS. 2 and 3, the blade guard 12 includes a sleeve shaped body 20. Body 20 has a reduced diameter base 21 that fits into an annular slot 22 in the front of the handpiece 14 located around the chuck 18. Slots 23 having an L-shape are formed in the end of the base 21. Pins internal to the handpiece, (pins not illustrated) seat in slots 23 (one shown) to couple the blade guard 12 to the handpiece 10.

A leg 24 extends forward from the exposed end of body 20. In the illustrated version of the invention, body 20 is formed with a transition section 26 having concave side walls 28 from which the leg 24 extends. Leg 24 is positioned so that when the blade guard 12 is installed, the lateral axis of the leg is aligned with the lateral axis of the saw blade 16.

Figure 3:
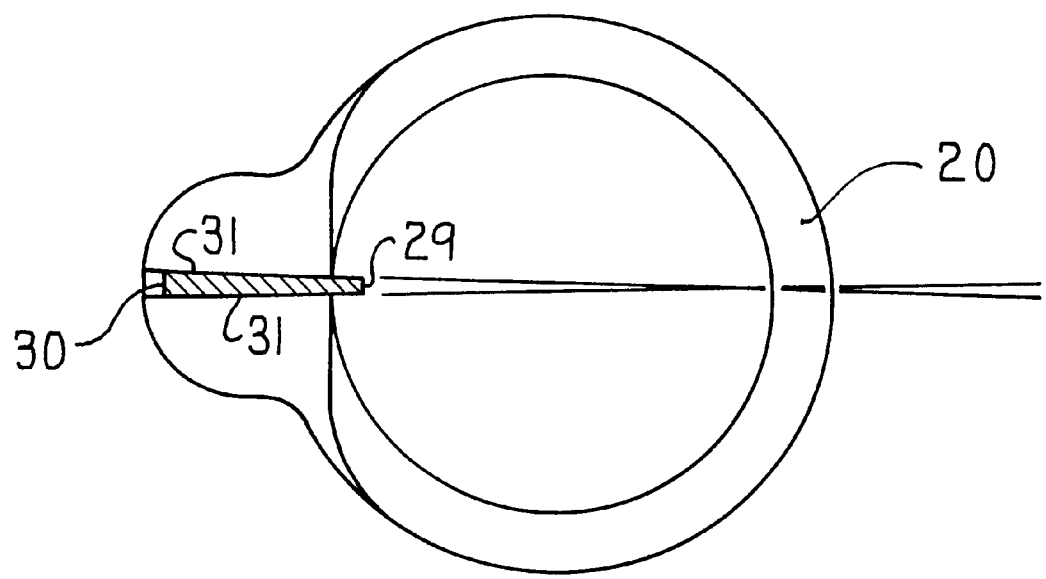
FIG. 3 is a cross sectional view of the leg of the blade guard taken along line 3—3 of FIG. 2.

As seen by the cross sectional view of FIG. 3, leg 24 is formed to have a wedge-shaped profile so that its leading edge 29, the edge closest to blade 16, is narrower in width than the trailing edge 30 which is distal from the blade. Leg 24 is further shaped so that the leading edge 29 is narrower in width than the associated saw blade 16. For example, in some versions of the invention in which the blade guard is employed with a sternum blade, it is anticipated that each side wall 31 of the leg will have a taper of between 0.5° and 2.0° relative to the lateral axis of the leg. In more preferred versions of the invention, this taper may be between 0.8° and 1.0°. In terms of dimensions, the width of the leading edge 29 of the leg may be between 15 and 35 mils; in more preferred versions of the invention, this width is between 20 and 30 mils. The width of the complementary trailing edge 30 of the leg 24 is, in preferred versions of this invention between 25 and 50 mils; in more preferred versions this width is between 35 and 45 mils.

A foot 34 is attached to the free end of the leg 24. The foot is formed with an opening 36 in which the free end of the saw blade 16 is seated. The foot 34, it will be observed, is significantly wider than the leg 24. For example, in some preferred versions of the invention foot 34 has a width between 200 and 300 mils; in more preferred versions the width is between 240 and 270 mils. The opening 36 is dimensioned so that the saw blade 16 can freely move within the foot 34.

The blade guard 12 of this invention is formed out of a single piece of metal. For example, it is anticipated the blade guard can be formed out of Martenistic stainless steel. This particular material is well suited to withstand autoclave sterilization. The blade guard 12 may be generally shaped by electronic discharge machine in which an electric current is employed to generate a cutting arc that forms the blade guard. After machining and deburring, it is anticipated the blade guard 12 will be electropolished. The post-formation processing of the blade guard 12 is performed to reduce the rate at which corrosion occurs.

Figure 4:
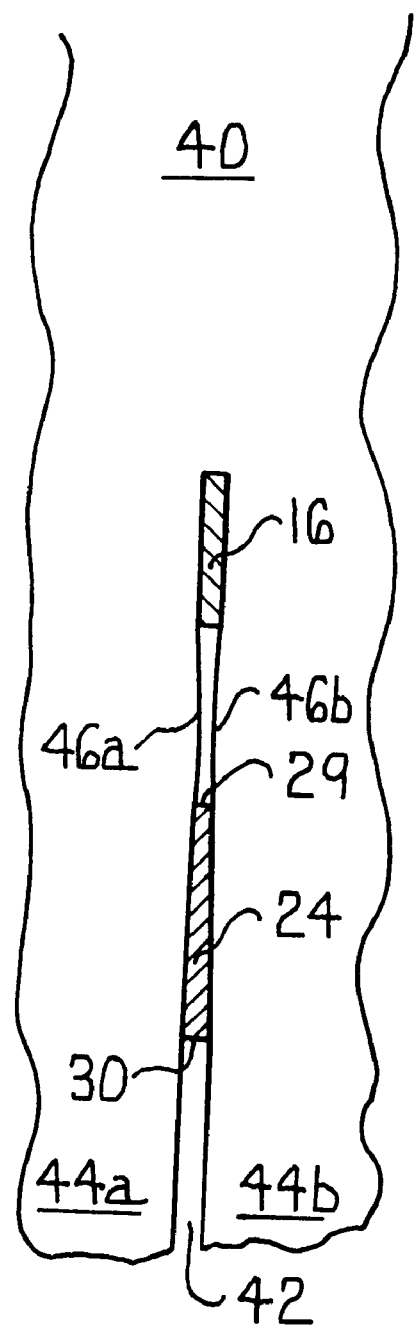
FIG. 4 is a top view depicting how bone is separate by a saw blade with which this blade guard is used and is held open by the blade guard.

The surgical saw 10 to which blade guard 12 is attached is employed in the normal manner. As depicted by FIG. 4, the saw 10 is positioned so that the blade 16 cuts into the bone 40 the saw is used to separate. This cutting forms an elongated void, a kerf 42, that separates the bone into two opposed sections 44a and 44b. The leg 24 of the guard, which is aligned with blade 16, travels in the kerf 42 so as to hold the guard foot 34 in line with the leg. Since the end of the blade 16 does not extend outside of the foot 34, the possibility that the blade will penetrate into the tissue underlying bone 40 is substantially reduced.

The wedge shaped profile of leg 24 facilitates the movement of the guard 12 with the saw 10. One reason for this is that the relatively wide trailing end provides the leg 24 with rigidity that prevents it from bending. This prevents the blade guard 12 from being bent out of shape and possibly abutting the blade 16. Since the leg 24 of the blade guard of this invention remains spaced from the blade 16, the noise and heat that is generated when these components come into contact is eliminated.

Moreover, since the leg 24 is wedge-shaped, it acts as wedge when it moves through the kerf. Thus, leg 24 forces the separated sections 44a and 44b of bone apart from each other as it moves through the kerf 42. This separation is desirable because, as seen by the opposed convex edges 46a and 46b of the bone, (shown exaggerated form for purposes of discussion) the separated bone has a tendency to close in on each other so as to narrow the width of the kerf 42. However, the separation of bone sections 44a and 44b by leg 24 limits this closing in of the kerf. Two advantages result from this separation. First, the holding of the kerf open minimizes the extent to which the opposed bone sections move in on the sides of both the saw blade 16 and kerf so as to impede forward cutting movement of the saw. Secondly, the holding apart of the bone sections 44a and 44b facilities the actual separation of the uncut bone 36 by the forward edge of the saw blade 16. These advantages are especially useful when the saw 10 is being employed to cut the bone in a non-linear pattern.

Thus, the blade guard 12 of this invention both facilitates its own use and the efficiency of the surgical saw 10 with which it is used.

It should be recognized that the foregoing description has been limited to one version of the invention. It will be apparent that variations can be made to this invention with the attainment of some or all of the advantages thereof. For example, while the disclosed blade guard 12 is intended for use with a sternum saw with a reciprocating blade 16, other blade guards of this invention may be designed for use with other cutting tools. For example, the blade guard may be used with other surgical saws that employ reciprocating blade, blades that move in sagittal pattern or blades that engage in oscillating or circular motion. Also, the blade guard of this invention may be used with rotating cutting bits such as those employed with duraguard cranial bone cutters.

It should also be realized that the blade guard of this invention can be used with other cutting tools such as cutters that employ light energy, lasers, or sonic energy.

Moreover, the blade guard of this invention may have a shape different from what has been described. The body may have a different shape in order to facilitate the coupling of the blade guard to the tool with which it is used. The shape of the foot may vary to facilitate the use of the blade guard with the blade or other cutting member with which the guard is used.

Also, the shape of the leg of the blade guard may vary from what has been described. For example, there is no requirement that the opposed sides of the leg both have an outwardly directed taper. In some versions of the invention, only one side of the leg may have this taper. Also, the taper need not always be linear. In some versions of the invention, the outwardly extending wall(s) of the leg may have a curved profile. The profile of this curve may be either convex or concave.

It should likewise be recognized that the leg may be shaped to have different trailing sections. For example, in some versions of the invention, the leg may have a diamond-shaped cross sectional profile. In these versions of the invention, the leg has a relatively narrow leading edge, a wide center portion and a narrow trailing edge. These versions of the invention may be useful for providing a guard that can be rearwardly moved out of the kerf through which it is traveling. The rearward taper of the leg facilitates the rearward movement of the guard through the kerf. Alternatively, the blade guard may have a tapered leading section followed by a constant-width trailing section. Moreover, it should be understood that the dimensions of the leg and foot may vary from what has been described.

Also, the material from which this blade guard is formed as well as the method of manufacture may vary from what has been descried. Therefore, it is an object of the appended claims to cover all such variations and modifications that come within the true spirit and scope of this invention.

The embodiments of the invention in which an exclusive property or privilege is claimed are defined as follows:

1. A method of cutting through a bone comprising the steps of:
   cutting through the bone with an elongated cutting member having a free end so as to form a kerf that extends through the bone and that is defined by two opposed sections of the bone;
   simultaneously with said cutting of the bone, moving a leg through the kerf, said leg having a wedge-shaped profile so that said leg separates the opposed sections of the bone defining the kerf from each other; and
   simultaneously with said cutting of the bone, encapsulating the free end of the cutting member in a foot attached to the leg so that the cutting member does not cut tissue located below the leg.

2. The method of cutting bone of claim 1, wherein the cutting member is a saw blade and said cutting of the bone is performed by sawing through the bone.

3. The method of cutting bone of claim 2, wherein the saw blade is actuated in a reciprocal pattern along a longitudinal axis to perform said cutting of the bone.

4. The method of cutting bone of claim 2, wherein:
   the saw blade has a width; and
   the leg is formed to have a leading edge that is proximal to the saw blade, a trailing edge that is distal from the saw blade and opposed side walls that extend between the leading edge and the trailing edge and, the leading edge has a width that is less than the width of the saw blade and the trailing edge has a width that is greater than the width of the leading edge.

5. The method of cutting bone of claim 4, wherein the side walls of said leg each have a linear profile.

6. The method of cutting bone of claim 4, where the side walls of the leg each has a taper.

7. The method of cutting bone of claim 6, where the taper of the side walls of the leg is between 0.5 and 2.0°.

8. The method of cutting bone of claim 1, wherein the leg moved through the bone has a leading edge adjacent the cutting member and a trailing edge distal from the cutting member and is formed with two opposed side walls that extend between the leading edge and the trailing edge, and the trailing edge is wider than the leading edge.

9. The method of cutting bone of claim 8, wherein the side walls of said leg each have a linear profile.

10. The method of cutting bone of claim 8, where the side walls of the leg each has a taper.

11. The method of cutting bone of claim 10, where the taper of the side walls of the leg is between 0.5 and 2.0°.

12. The method of cutting bone of claim 8, wherein the leading edge of the leg has a width between 0.015 and 0.035 inches.

13. The method of cutting bone of claim 12, wherein the trailing edge of the leg has a width between 0.025 and 0.050 inches.

14. The method of cutting bone of claim 8, wherein the trailing edge of the leg has a width between 0.025 and 0.050 inches.

15. A method of cutting bone comprising the steps of:
   cutting through the bone with a saw blade having a free end and a selected width so as to form a kerf that extends through the bone and that is defined by two opposed sections of the bone;
   simultaneously with said cutting of the bone, moving a leg through the kerf, the leg having a leading edge adjacent the saw blade, a trailing edge distal from the saw blade and opposed sides that extend between the leading edge and the trailing edge, wherein the leading edge has a width less than the width of the saw blade and the trailing edge has a width greater than the width of the saw blade; and
   simultaneously with said cutting of the bone, encapsulating a free end of the saw blade in a foot attached to the leg so that the free end of the saw blade not cut tissue.

16. The method of cutting bone of claim 15, wherein the side walls of said leg each have a linear profile.

17. The method of cutting bone of claim 15, where the side walls of the leg each has a taper.

18. The method of cutting bone of claim 17, where the taper of the side walls of the leg is between 0.5 and 2.0°.

19. The method of cutting bone of claim 15, wherein the leading edge of the leg has a width between 0.015 and 0.035 inches.

20. The method of cutting bone of claim 15, wherein the trailing edge of the leg has a width between 0.025 and 0.050 inches.

21. The method of cutting bone of claim 15, wherein the saw blade is moved in a reciprocating pattern.

22. The method of cutting bone of claim 15, wherein the saw blade is actuated by a powered device.

* * * * *